United States Patent [19]

Prager

[11] 4,257,416
[45] Mar. 24, 1981

[54] MULTI-CHANNEL VENIPUNCTURE INFUSION SET

[76] Inventor: David Prager, 1394 N. 39th Street, Allentown, Pa. 18104

[21] Appl. No.: 35,608

[22] Filed: May 3, 1979

[51] Int. Cl.³ .............................................. A61M 5/00
[52] U.S. Cl. ........................... 128/214 R; 128/214 G; 128/214.2
[58] Field of Search .......... 128/214 R, 214 B, 214 D, 128/214 G, 214.2, 227, DIG. 26, 760–767

[56] References Cited

U.S. PATENT DOCUMENTS

| | | | |
|---|---|---|---|
| 2,656,835 | 10/1953 | Eisenstein | 128/214 G |
| 2,674,265 | 4/1954 | Dennis | 128/213 X |
| 3,677,242 | 7/1972 | Shaye | 128/214 C |
| 3,782,382 | 1/1974 | Naftulin et al. | 128/214 R |
| 3,886,937 | 6/1975 | Bobo et al. | 128/214 G |
| 3,941,126 | 3/1976 | Dietrich et al. | 128/214 G |
| 3,957,082 | 5/1976 | Fuson et al. | 128/214 R X |

Primary Examiner—Dalton L. Truluck
Attorney, Agent, or Firm—Ronald B. Sherer

[57] ABSTRACT

A multi-channel venipuncture infusion set is disclosed for simultaneously dispensing multiple, intravenous solutions, parenteral fluids and drugs, and which also permits withdrawal of blood samples without disconnecting the infusion set from the dispensing sources and without removing or replacing the venipuncture needle in the patient.

10 Claims, 4 Drawing Figures

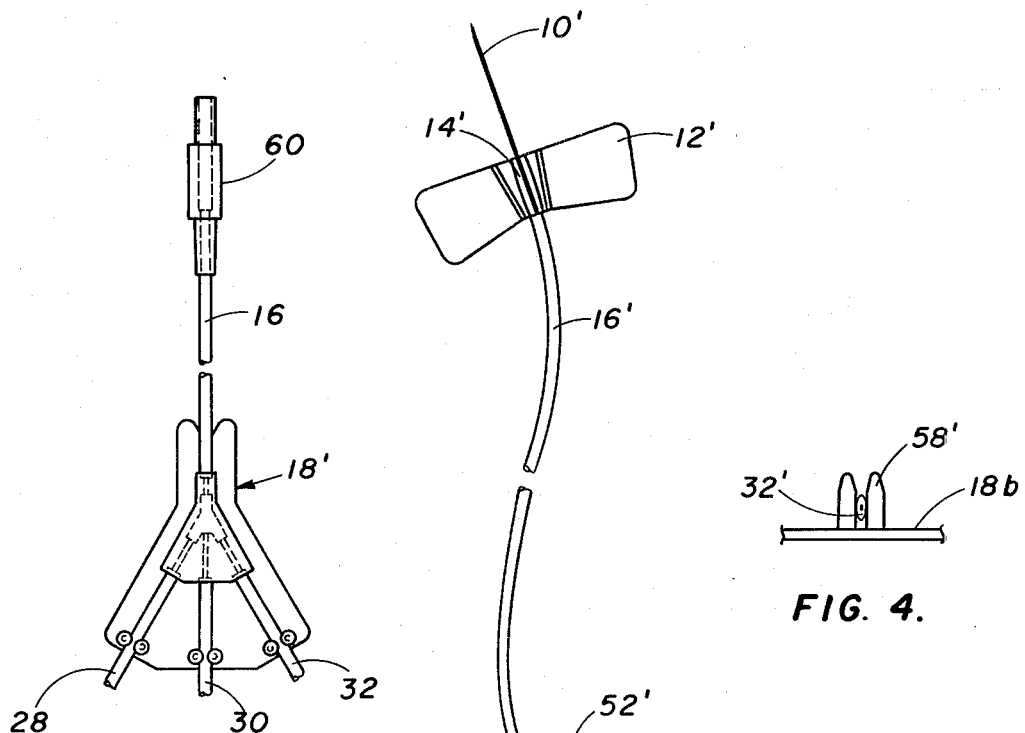
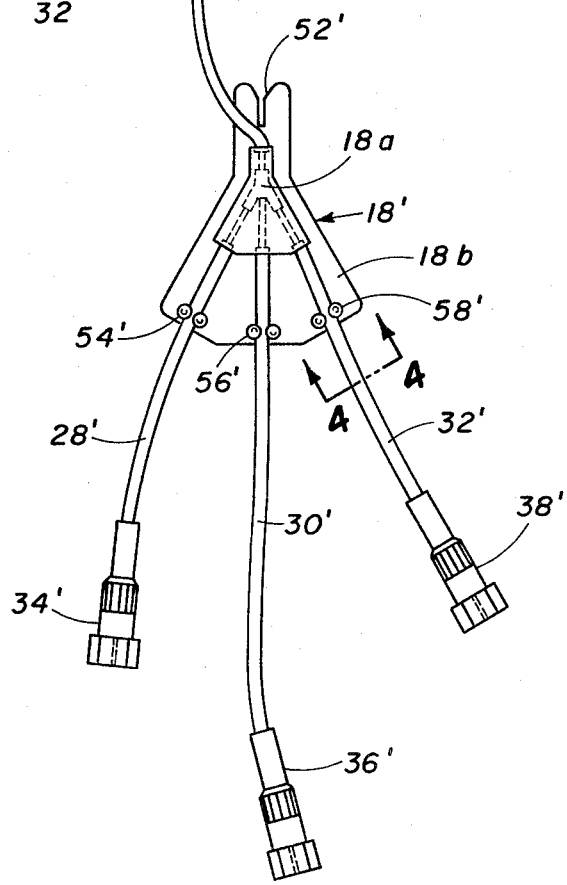
FIG. 3.
FIG. 4.
FIG. 2.

MULTI-CHANNEL VENIPUNCTURE INFUSION SET

BACKGROUND OF THE INVENTION

While various types of medical tubing arrangements have been previously devised, particularly for withdrawing blood from donors and replacing the red cells such as shown in U.S. Pat. No. 3,782,382, there has long been a need for an improved and simplified infusion set whereby at least two different drugs may be simultaneously administered to a patient, while also permitting the withdrawal of blood samples from the patient without completely disconnecting the infusion set from the source of medication, and without removing and replacing the needle from the patient's vein. In this regard, all previous intravenous infusion sets of which I am aware have been composed of a single length of tubing extending from the venipuncture needle and terminating a female adaptor which connects the single tube to a source of medication or other intravenous fluid.

Alternatively, plastic Y-fittings have been attempted in order to provide a secondary means of injecting a second drug as by inserting a needle from a second drug source through a self-sealing portion of the Y-fitting. However, this limits the use of the infusion set to the number of Y-fittings, and requires disconnection and/or removal from the patient in order to withdraw a blood sample.

SUMMARY OF THE INVENTION

The present invention provides a single venipuncture needle which is inserted in the patient's vein and from which the needle tube extends to a multi-passage manifold from which a plurality of separate inflow tubes are connected. Each one of the multiple inflow tubes terminates in a standard, female connector which receives either the male adaptor end of an intravenous tube attached to a standard infusion bag or bottle, or the male adaptor end of a syringe. The outflow needle tube and the individual inflow tubes are provided with pinch-type closure members which enable each of the multiple tubes to be individually opened or closed to the flow of fluids to and/or from the patient.

BRIEF DESCRIPTION OF THE DRAWINGS

FIG. 2 is a top, plan view of a second embodiment of the present invention including one preferred form of closure means;

FIG. 3 is a top, plan view showing an alternative form of the present invention in which the needle tube terminates in a male lock-type adaptor instead of a needle; and FIG. 4 is a fragmentary cross-sectional view taken along view lines 4—4 of FIG. 2.

DETAILED DESCRIPTION

Figure 1:
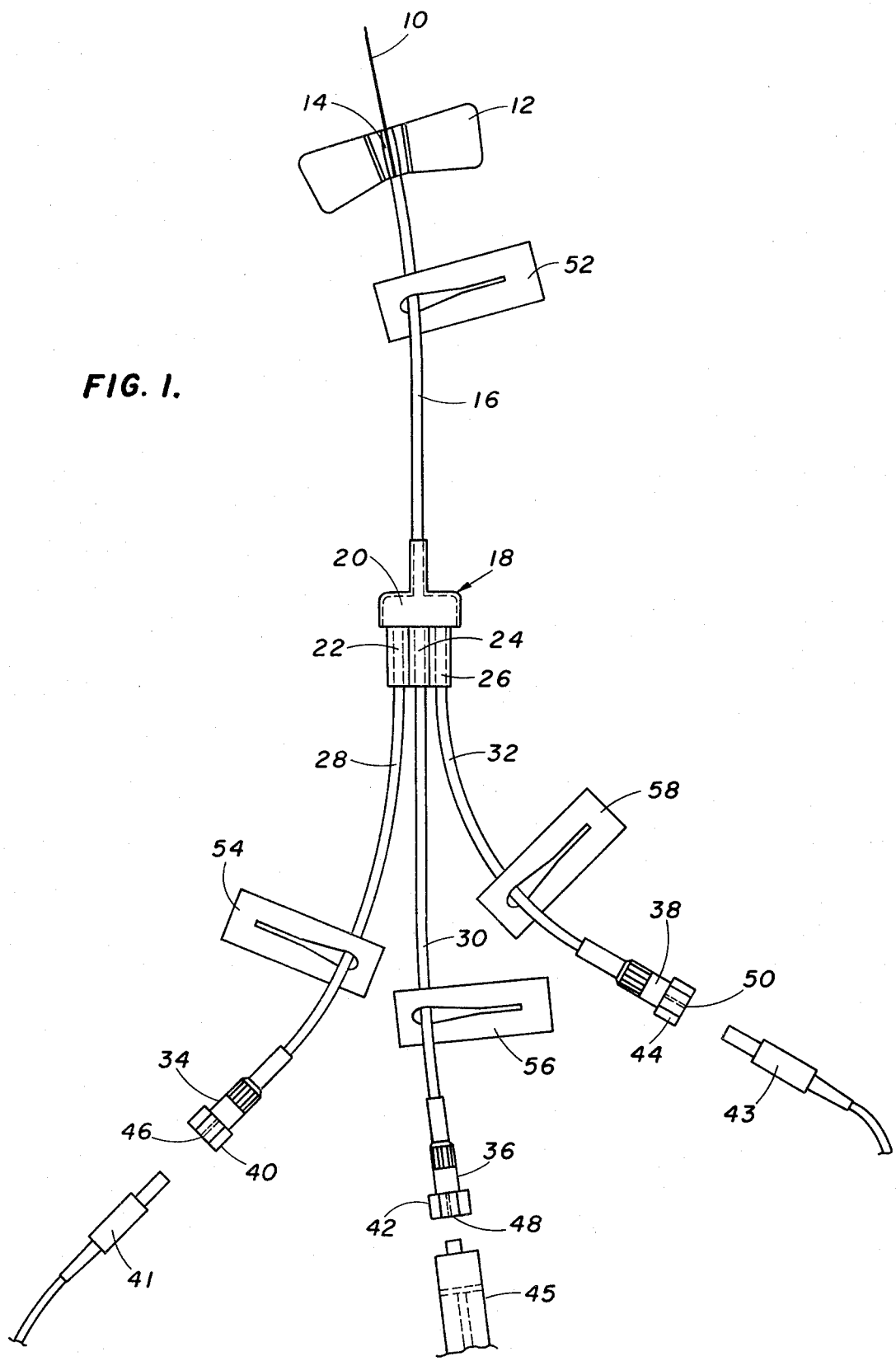
FIG. 1 is a top, plan view showing a first embodiment of the present invention.

Referring to FIG. 1, the first embodiment of the multi-channel infusion set comprises a standard venipuncture needle 10 which is adapted to be inserted into the patient's vein by means of grasping the flexible wing tabs 12 secured to the base of the needle adaptor 14. This needle and tab structure is conventional, and it will be understood that adaptor 14 connects needle 10 to a first tube 16 which is hereafter referred to as the needle tube. Needle tube 16 terminates at its opposite end in a multi-passage manifold 18, which is preferably composed of an inert plastic material, and which includes a mixing manifold passage 20 in open communication with inflow passages 22, 24, and 26. Passages 22, 24, and 26 are respectively connected to inflow tubes 28, 30 and 32 which terminate in standard flanged female adaptor plugs 34, 36 and 38. It will be noted that adaptors 34, 36 and 38 are illustrated as having vented closure caps 40, 42 and 44 including small vent holes 46, 48 and 50 the function of which will hereinafter be explained.

As further shown in the FIG. 1 embodiment, the present invention may utilize closure members in the form of slide clamps 52, 54, 56 and 58 having wedge-type slots which may be positioned so as to pinch the tubing in the narrow portion of the slot. Such slide clamps are known per se, and more particularly described in U.S. Pat. No. 3,316,935.

In use, all of the slide clamps are first moved to their open position, except slide clamp 52 which is in the closed position. Cap 42 is removed in a sterile manner, and a standard syringe with a female end is inserted into adaptor 36. Such syringe contains a diluent of choice such as normal saline. This diluent of choice is forced into tube 30, through passage 24, through manifold 20, and through passages 22 and 26 into tubes 28 and 32 in order to remove the air from the system which is vented through the vent caps 40 and 44. Slide clamps 54 and 58 are then placed in their closed positions. Then slide clamp 52 is placed in the open position, and the diluent from the attached syringe on tube 30 is then forced into tube 16 until the diluent is forced through the end of needle 10 in order to clear air from tube 16. Slide clamp 52 is then placed in the closed position, and the needle is inserted into the patient's vein. Alternatively, instead of using a syringe with the diluent of choice, any standard intravenous solution in bottle or bag form may be attached to adaptor 36 by removing cap 42 and proceeding in a like manner.

The operator of the present invention may now attach to adaptors 34 and 38, in either a selective or dual manner, the medicant or solution of choice for intravenous insertion into the patient. This may be done simultaneously or intermittently with or without precharged syringes. For example, selectively, the intravenous medication or solution attached to adaptor 34 can be administered intravenously by pressure, gravity or by a hand-activated system such as a pre-filled syringe. This is done by opening clamp 54, closing slide clamps 56 and 58, and opening clamp 52. For simultaneous multi-fluid administration, the second source of solution or medication can be attached to adaptor 38 at the same time that the attachment is made to adaptor 34. Once the fluid of choice is administered through tube 28 past manifold 20 into tube 16 through the needle 10 into the patient's vein, then slide clamp 54 is closed, slide clamp 56 is opened, and the system is flushed with a diluent of choice. Then slide clamp 56 is closed, slide clamp 58 is opened, and the second fluid of choice is passed through tube 32 and manifold 20 into tube 16 and into the patient's arm through needle 10. Following that, slide clamp 58 is closed, slide clamp 56 is opened and the system is flushed with the diluent of choice. The system may remain intact for up to 72 hours with slide clamp 54 closed, slide 58 closed, slide clamp 56 open and slide clamp 52 open while the intravenous medication or fluid is administered through the adaptor 36, line 30 and into the patient's vein.

The multi-channel venipuncture infusion set as shown in FIG. 1 may also be used as a multi-channel solution set wherever there is a need to simultaneously administer multiple solutions intravenously including the induction and maintenance of anethesia by anesthetic fluids. Also, this system permits self-administration of Factor 8 or Factor 9 concentrates that are commercially available to patients with hemophilia who are on a strictly administered self-care home program. The technique for use of the multi-channel infusion set for patient self-administration under medical guidance first involves removing the sterile product from the package. The whole system is then primed to remove any air from the system. This is accomplished by first placing clamp 52 in the closed positon. Factor 8 or Factor 9 concentrate or cryoprecipitate of choice is then attached to adaptor 36 after removing cap 42. By hand pressure, the solution is then passed into tube 30 through manifold 20 and then into tubes 28 and 32, with slide clamps 54 and 58 in the open position, until the solution appears at the vented caps 40 and 44. Appropriate dosages of pre-charged syringes of concentrate or diluent of choice are attached to the flanged adaptors 34 and 38. Clamps 54 and 58 and then placed in the closed position and, with hand pressure upon the syringe attachment or intravenous bag or bottle attached to adaptor 36, air is removed from tube 16 through the needle point 10. The patient then performs the venipuncture in the appropriate anatomical area, be it the antecubital fossa or hand, with the attached medications on any of the previously designated adaptors 34, 36 or 38. After assuring adequacy of the patient's vein, then by utilizing hand pressure upon the syringe, or by gravity feed from a bag higher than the venous pressure of the patient, the diluent of choice or replacement concentrate passes from syringe 45 into adaptor 36 to tube 30 through passage 24 and manifold 20 into tube 16 and through needle 10 into the patient's vein. Upon completion of that circuit, clamp 56 is then closed, clamp 54 is then opened, and the parenteral fluid of choice passes through adaptor 34 into tube 28, through passage 22 into manifold 20 and through tube 16 and needle 10 into the patient's vein. Then, clamp 54 is closed and clamp 58 is opened and, if there is parenteral fluid attached to adaptor 38, then by gravity or hand pressure, the fluid is forced through adaptor 38, tube 32, passage 26, manifold 20, tube 16 and through the tip of needle 10 into the patient's vein. Then, slide clamp 58 is placed in the closed positon, and slide clamp 56 is placed in the open position, and the primer diluent of choice is discharged into the system by hand or gravity feed through adaptor 36, tube 30, passage 24, manifold 20, tube 16 and through needle 10 into patient's vein. After the completion of the administration of the Factor 8 or Factor 9 concentrate or cryoprecipitate, the whole system is removed from the patient's vein by grasping tab 12 and applying pressure to the venipuncture site.

In an additional mode of operation, prior to utilizing the embodiment of FIG. 1 to administer any fluid to the patient, a sample of venous blood may be obtained for quantitative analysis. This may be accomplished by first removing the multi-channel infusion set from the sterile package. Clamps 54 and 58 are closed and a syringe is attached to adaptor 36. Clamp 52 is opened and the venipuncture is performed in a standard manner utilizing tab 12 with needle 10. When venous patency is ascertained, suction is applied through the attached syringe on adaptor 36, and blood is drawn through needle 10 into tube 16, manifold 20, through passage 24 and tube 30 into adaptor 36 and into the syringe 45. When the appropriate volume of blood has been removed, then clamp 56 is closed and a pre-charged syringe of the medication of choice may be attached to adaptor 34 or 38 with clamp 52 open. If the syringe is to be attached to adaptor 34, then suction is first placed on line 28 which draws blood from tube 16 which removes air from passage 22 and line 28. Then, one may attach and administer the medication of choice through line 28, passage 22, manifold 20 and line 16 through needle 10 into the patient's vein. The same technique as just mentioned can also then be accomplished through line 32 by attaching the medication in a syringe, or other intravenous solution source, to adaptor 38. Then, by opening clamp 58, closing clamp 56 and closing clamp 54, a different fluid may be administered through tube 32, passage 26, manifold 20 and tube 16 through needle 10.

Referring now to FIG. 2 of the drawings, the most preferred embodiment of the present invention will be described using the same numerals with primes to indicate the corresponding elements of the first embodiment just described. The preferred embodiment includes the same arrangement of needle 10', wing tabs 12' and needle tube 16' as previously described, as well as, the same arrangement of three separate inflow tubes 28', 30' and 32' having female adaptors 34', 36' and 38'. The distinction from the FIG. 1 embodiment resides in the particular design of multi-passage manifold 18' which may be manufactured as two separate elements comprising a base plate 18b and a molded or bored multi-passage manifold block 18a. After the base plate 18b and the block 18a are separately manufactured, these two components are then joined as by plastic snap-pins, or by fusion type gluing, or by other suitable means.

Base plate 18b preferably includes a plurality of pairs of tapered pins which form pinch-type closure means as more clearly illustrated in FIG. 4. Alternatively, one or more of the pinch-type closure may be formed by providing tapered slots, such as slot 52', in base plate 18b. In this manner, all of the slide clamps of the first embodiment are eliminated, and the tubes are individually pinched closed either by inserting the respective tube in its respective slot, such as slot 52', or by wedging the individual tubes between the tapered posts 54', 56' or 58', as most clearly shown in FIG. 4. Since the manner of operation is identical to that previously described with respect to FIG. 1, it will be apparent that the FIG. 2 embodiment provides the same multiplicity of modes of operation as previously described.

As shown in FIG. 3, the needle tube from either of the FIG. 1 or FIG. 2 embodiments may terminate in a male lock-type adaptor 60 instead of the previously described venipuncture needle 10. Therefore, it will be apparent that either of the previously described embodiments of the invention may be utilized in connection with previous type of single-tube infusion sets so as to convert the latter to the multiple uses provided by the present invention.

While FIG. 2 illustrates the clamping slot 52' and posts 54', 56' and 58' as being formed in base plate 18b, it will be apparent that the posts may be formed as integral portions of the connector block 18a, or base plate 18b may be in the form of an integral flange extending outwardly from the block and being provided with wedge-type slots and/or the pairs of tapered posts. It should also be understood that, while the slide clamps and wedge slots are very effective in closing the tubes, the use of the pairs of tapered posts is preferred from the standpoint of ease of use and less bending of the tubes which reduces the chance of movement of the needle in the patient.

It will also be apparent that the size of the tubing of the present invention may be either the micro size having internal diameters in the orders of 0.040 to 0.070 inches, or of the macro size having internal diameters in the orders of 0.105 to 0.110 inches. In addition, the present invention may be composed of a relatively short needle tube 16, such as in the order of 6 inches when the invention is used as above-described in connection with the administration of chemo-therapy drugs or other parenteral solutions. However, it is also to be understood that the present invention may be constructed with a much longer needle tube 16, such as in the order of 12 to 36 inches, where by a patient may self-administer certain drugs such as in a case of hemophiliacs or for the administration of parenteral solutions. That is, with the longer needle tube 16, or 16', the patient may insert the needle in the vein in his arm, and then have both hands free to connect the adaptors to the medication to be self-administered and to operate the various wedge-type clamps.

It will be understood that, in addition to the above-described modes of operation, the present invention provides the capability of pre-filling a number of syringes, or other containers of parenteral fluids such as bags or bottles, with pre-measured doses of the fluids to be administered. These may be pre-connected to the adaptors at the hospital pharmacy, or even at a drug store for some medications, such that the complete infusion set is then ready to be administered by a nurse, or self-administered, with only a single venipuncture procedure.

From the foregoing description of two embodiments of the present invention, it will be apparent that multiple drug administration and withdrawal of blood samples is made possible without disconnecting the infusion needle from the patient, and that the present invention provides a significantly greater flexibility in the modes of use that has been previously possible. It will also be understood that the foregoing description is intended to be illustrative of the principles of the invention, and that the present invention is not intended to be limited other then as set forth in the following claims.

What I claim is:

1. A multi-channel infusion set comprising a multiple passage manifold having first, second, third and fourth passages in permanently open communication, a venipuncture needle tube connected to said first manifold passage, at least three inflow tubes having one end thereof connected to said second, third and fourth manifold passages, respectively, female flanged adaptors connected to the opposite ends of each of said inflow tubes, and pinch-type closure means operatively associated with each of said needle tube and inflow tubes for selectively pinching each of said tubes closed.

2. The multi-channel infusion set as claimed in claim 1 in which said manifold comprises a multi-passage portion and a plate portion, and said closure means are permanently secured to said plate portion.

3. The multi-channel infusion set as claimed in claim 1 in which said closure means are integral with said multiple passage manifold.

4. The multi-channel infusion set as claimed in claim 1 in which said female adaptors include removable caps, and said caps include vent means.

5. The multi-channel infusion set as claimed in claim 3 in which at least some of said closure means comprise pairs of tapered posts.

6. The multi-channel infusion set as claimed in claim 3 in which at least some of said closure means comprise a wedge-type slot.

7. The multi-channel infusion set as claimed in claim 3 in which some of said closure means comprise pairs of tapered posts and at least one of said closure means comprises a wedge-type slot.

8. The multi-channel infusion set as claimed in claim 1 in which said venipuncture needle tube terminates in a male lock type adaptor having a size and shape such as to be received in the female adaptor of a conventional, single-tube infusion set.

9. A method of administering multiple parenteral fluids into a patient's vein through a single multi-channel infusion set including a needle tube having one end connected in permanently open fluid communication with at least two initially open inflow tubes comprising:
    (a) closing said needle tube to the passage of fluid there through,
    (b) passing a first fluid into and through one of said open inflow tubes and out through the other of said open inflow tubes to vent the air from both of said inflow tubes,
    (c) closing said other inflow tube,
    (d) opening said needle tube and passing said first fluid through said needle tube to vent the air therefrom,
    (e) connecting said needle tube to said patient's vein,
    (f) administering a first parenteral fluid through one of said inflow tubes and said needle tube into said pateint's vein,
    (g) opening said other inflow tube, and
    (h) administering a second parenteral fluid through said second inflow tube and said needle tube into said patient's vein.

10. The method as claimed in claim 9 in which, said multi-channel infusion set includes a third inflow tube, and said method includes venting air from all three of said inflow tubes by passing said fluid in step (b) into one of said inflow tubes and out through both of the other two inflow tubes, and thereafter administering at least two parenteral fluids into said patient's vein through two of said inflow tubes.

* * * * *